US00PP16662P2

(12) United States Plant Patent
Holland

(10) Patent No.: US PP16,662 P2
(45) Date of Patent: Jun. 13, 2006

(54) LILAC PLANT NAMED 'BAILINA'

(50) Latin Name: *Syringa meyeri×Spyringa microphylla*
Varietal Denomination: Bailina

(75) Inventor: Neal S. Holland, Harwood, ND (US)

(73) Assignee: Bailey Nurseries, Inc., St. Paul, MN (US)

( * ) Notice: Subject to any disclaimer, the term of this patent is extended or adjusted under 35 U.S.C. 154(b) by 84 days.

(21) Appl. No.: 11/116,458

(22) Filed: Apr. 28, 2005

(51) Int. Cl.
*A01H 5/00* (2006.01)

(52) U.S. Cl. ..... Plt./248
(58) Field of Classification Search ..... Plt./248
See application file for complete search history.

(56) References Cited

U.S. PATENT DOCUMENTS

PP12,294 P2 * 12/2001 Holland ..... Plt./248
PP15,152 P2 * 9/2004 Holland ..... Plt./248
PP15,588 P2 * 2/2005 Holland ..... Plt./248
2005/0172376 P1 * 8/2005 Holland ..... Plt./248

OTHER PUBLICATIONS http://www.heardgardens.com/lilacinventory.htm.*
http://www.baileynursery.com/bnf/newsitems/04102001_4.asp.*

* cited by examiner

*Primary Examiner*—Kent Bell
*Assistant Examiner*—W. C. Haas
(74) *Attorney, Agent, or Firm*—Buchanan Ingersoll PC

(57) ABSTRACT

A new and distinct highly ornamental cultivar of *Syringa meyeri×Syringa microphylla* is provided. A Lilac plant having a generally rounded to oval uniform compact dwarf growth habit is described. Highly attractive densely packed trusses of intensely sweet smelling medium pink buds that open to light pink florets are formed in late spring and subsequently fade to almost white at maturity. Good winter hardiness is made possible and the plant has been found to be relatively free of insect and disease problems during observations to date particularly when grown in full sun in well drained soil. The plant is suitable for growing in U.S.D.A. Hardiness Zone Nos. 4 to 7. The plant is well-suited for growing as an ornamental specimen or as a mass planting in the landscape. The plant also can be grown as a foundation planting or as an informal hedge.

1 Drawing Sheet

Botanical/commercial classification: *Syringa meyeri× Spyringa microphylla*/Ornamental Lilac Shrub.
Varietal denomination: cv. 'Bailina'.

SUMMARY OF THE INVENTION

The new Lilac plant of the present invention was created at Harwood, N.Dak., U.S.A., by the cross of *Syringa meyeri* 'Palibin' (non-patented in the United States) and *Syringa microphylla* 'Superba' (non-patented in the United States). The parentage can be summarized as follow:

'Palibin'×'Superba'.

Seeds from the cross were collected during 1976, were planted, and the resulting plants were observed. A single plant of new cultivar was selected during 1985 in view of its distinctive combination of ornamental characteristics. This plant initially was designated No. 92-2.

It was found that the cultivar of *Syringa meyeri×Syringa microphylla* exhibits the following combination of characteristics:

(a) exhibits generally rounded to oval uniform compact dwarf growth habit, (b) forms in late spring densely packed attractive trusses of intensely sweet smelling medium pink buds that open to light pink florets that fade to almost white at full maturity, (c) is relatively free of insect and disease problems, and (d) is well-suited for growing as a distinctive ornamental shrub in the landscape.

The new cultivar of the present invention provides a distinctive blossom coloration and fragrance to the landscape that are displayed in late spring after many other shrubs have finished flowering. The generally rounded to oval growth habit commonly assumes a height and width of approximately 5 to 6 feet at maturity. The new plant can be grown to advantage as a specimen shrub or in a mass planting. The plant is versatile for many uses in the landscape including foundation plantings, and informal hedges. The superior hardiness of the *Syringa meyeri* 'Palibin' parent which generally is lacking in the *Syringa microphylla* 'Superba' parent is imparted to the new cultivar of the present invention. The new cultivar performs best when grown in full sun in well-drained soil.

The new cultivar of the present invention can be readily distinguished from its parental cultivars. More specifically, the 'Palibin' cultivar exhibits reddish-purple buds that open to pale lilac flowers, and the 'Superba' cultivar exhibits an often taller and considerably more spreading growth habit and forms deep pink blossoms. The 'Palibin' cultivar commonly reaches a height of approximately 4 to 5 feet and width of approximately 5 to 7 feet. The 'Superba' cultivar commonly reaches a height of approximately 6 feet and a width of approximately 9 to 12 feet.

The new cultivar of the present invention also can be readily distinguished from other Lilac cultivars, such as 'Bailbelle' (U.S. Plant Pat. No. 12,294), 'Baildust' (U.S.

Plant Pat. No. 15,152), 'Bailsugar' (U.S. Plant Pat. No. 15,588), and 'Bailming' (U.S. Plant patent application Ser. No. 10/769,779, filed Feb. 3, 2004), resulting from the same breeding program in view of the distinctive blossom coloration. More specifically, the 'Bailbelle' variety forms pink blossoms, the 'Baildust' variety forms pale antique pink blossoms, the 'Bailsugar' variety forms purple lilac blossoms, and the 'Bailming' cultivar forms red purple blossoms that fade to lavender pink. The light pink blossoms of the new cultivar are also more fragrant than those of the above-identified varieties.

The new cultivar of the present invention was asexually propagated by the use of rooted cuttings and grafting at St. Paul, Minn., U.S.A., during 1992, and the progeny were field planted during 1993. The distinctive characteristics of the new cultivar have been found to be stable and to be capable of transmission from one generation to another following such asexual propagation at St. Paul, Minn., U.S.A., and elsewhere. The new cultivar reproduces true to type in successive generations of asexual reproduction.

The new cultivar grows well from rooted cuttings that are subsequently grown outdoors in a production field and then are transferred to containers at St. Paul, Minn., U.S.A., and at Yamhill, Oreg., U.S.A. The new cultivar can be marketed as rooted cuttings, bareroot plants, and as container grown plants.

The new cultivar of the present invention also has been grafted on *Syringa reticulata* to form distinctive small grafted trees.

The new cultivar of the present invention has been named 'Bailina'. It is a member of the FAIRYTALE™ Series of Lilac plants that includes the 'Bailbelle' 'Baildust', 'Bailsugar', and 'Bailming' cultivars, and is being marketed under the THUMBELINA trademark.

BRIEF DESCRIPTION OF THE PHOTOGRAPHS

The accompanying photographs show, as true as reasonably possible to make the same in color illustrations of this character typical plants of the new cultivar. The plants were propagated by use of rooted cuttings and were photographed when approximately three years of age during 2003 and 2004 while growing outdoors during late spring at St. Paul, Minn., U.S.A.

DETAILED DESCRIPTION

Figure 1:
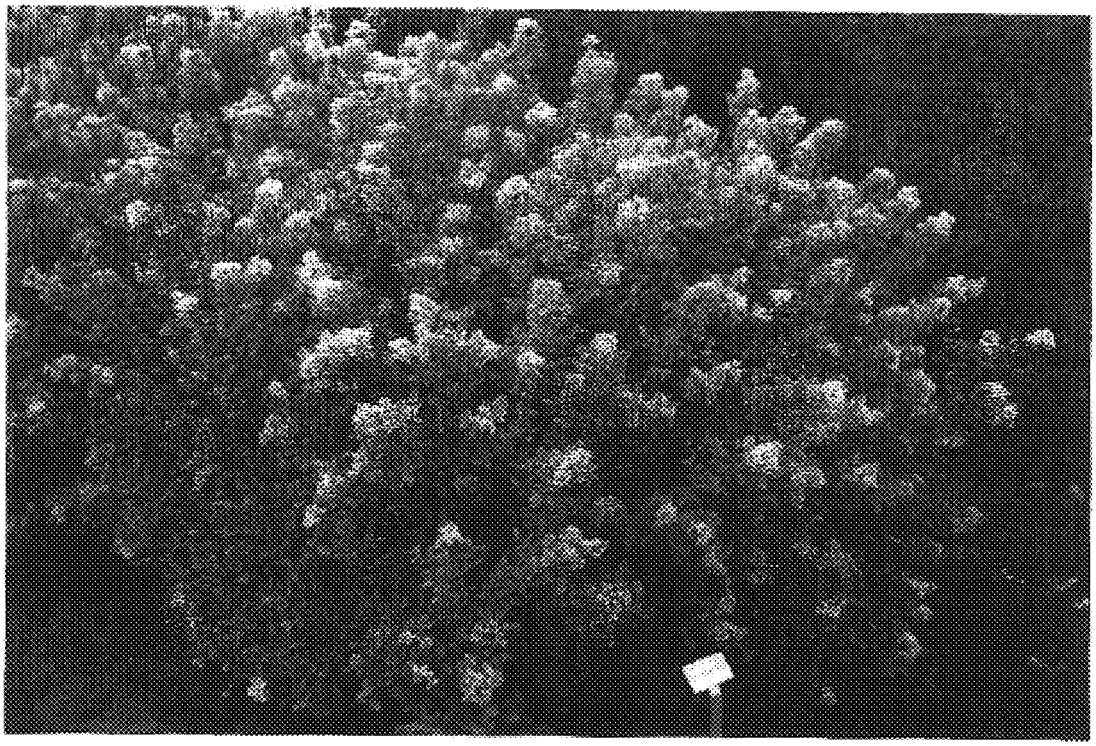
FIG. 1 shows a blossoming plant wherein the generally rounded to oval uniform and compact growth habit of the new cultivar is exhibited.
Figure 2:
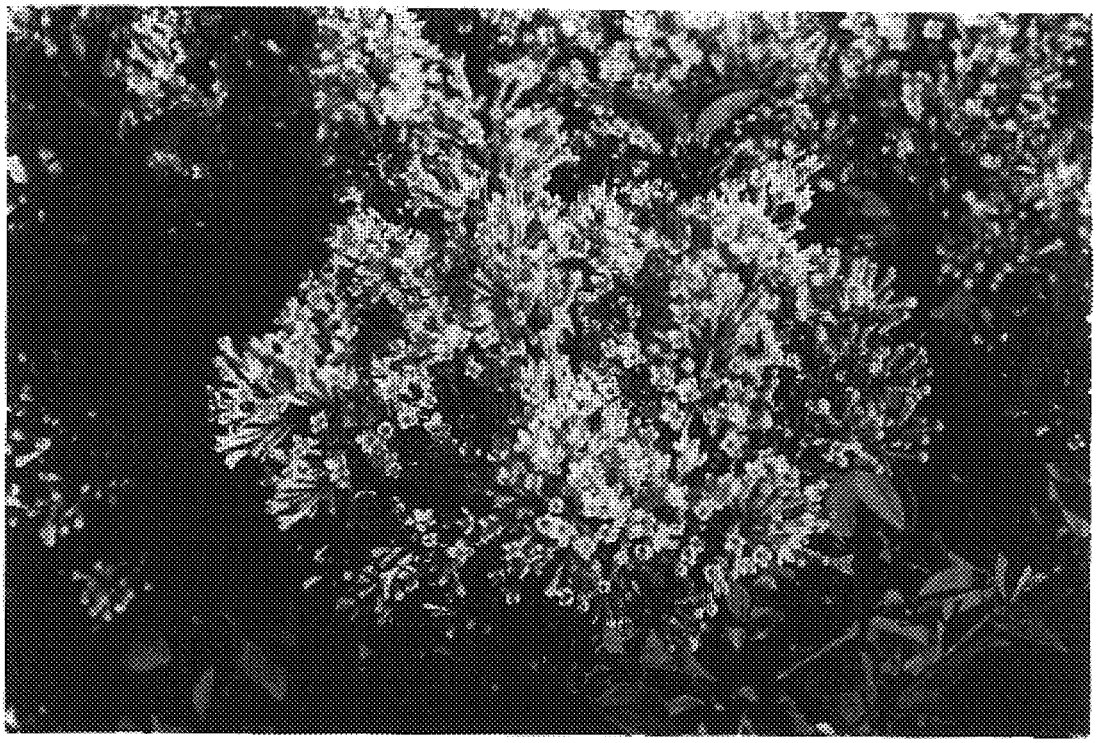
FIG. 2 shows a closer view of the medium pink buds that open to light pink florets that fade to near white at maturity, as well as the foliage.

The chart used in the identification of colors is The R.H.S. Colour Chart of The Royal Horticultural Society, London, England. Common terms are to be accorded their ordinary dictionary significance. The description is based upon the observation during May and July 2003 and 2004 of two and five year-old plants propagated by the use of rooted cuttings and growing outdoors in containers and in the field at St. Paul, Minn., U.S.A.

Botanical classification: *Syringa meyeri*×*Syringa microphylla,* cv. 'Bailina'.

Plant:

*Growth habit.*—Neat compact generally rounded to oval dwarf shrub, and a uniform grower.

*Size.*—Forms a shrub of approximately 1.5 to 1.8 m (approximately 5 to 6 feet) in height and approximately 1.25 to 1.8 m (approximately 5 to 6 feet) in width.

Bark:

*Texture.*—Glabrous.

*Color.*—Greyed-Green Group 197D.

Foliage:

*Leaf shape.*—Elliptic/ovate.

*Arrangement.*—Opposite.

*Leaf apex.*—Acute to obtuse.

*Leaf base.*—Rounded.

*Leaf surface.*—Matte.

*Leaf margins.*—Entire.

*Venation.*—Palmately-veined.

*Leaf length.*—Approximately 3 cm on average.

*Leaf width.*—Approximately 2 cm on average.

*Color young foliage.*—Commonly between Green Group 138B and Green Group 139C on the upper surface, and near Green Group 139C on the under surface.

*Color adult foliage.*—Commonly near Green Group 138A on the upper surface, and near Green Group 138B on the under surface.

*Petioles.*—Green Group 137D with highlights of Greyed-Purple Group 185B on the upper surface, Green Group 139C on the under surface, approximately 0.7 cm in length on average, and approximately 0.15 cm in diameter on average.

*Stems.*—Green Group 138A on young stems, and Greyed-Green Group 197C with highlights of Yellow-Green Group 148B on adult wood.

*Lenticels.*—Commonly are present on stems, Grey-Brown Group 199D in coloration, and approximately 0.2 cm in size on average.

Inflorescence:

*Age to flower.*—Typically the first flowers appear the second year from a rooted cutting in the field and in container production. A few flowers have been observed during the first year depending upon the time of planting.

*Time of flowering.*—Typically mid- to late-May at the indicated location. Such flowering commonly is after many other flowering shrubs have finished blooming.

*Buds.*—In trusses, closed funnel-form, red purple, Red-Purple Group 62C (upper surface), and between Red-Purple Group 62B and 62C (under surface). The length commonly is 1.3 cm on average and the width approximately 0.25 cm on average.

*Flower arrangement.*—Densely packed in panicles or trusses.

*Flower configuration.*—Tubular with four petal lobes at the end (as illustrated).

*Flower size.*—Approximately 1.0 cm in length on average and approximately 0.3 cm in diameter on average at the widest point.

*Flower color.*—When first opening the petals are Red Group 56C (upper surface) and Red Group 54C (under surface). When blooming the petals are Red Group 56D (upper surface) and between Red Group 56A and 56B (under surface). At the end of blooming the petals are lighter than Red Group 56D at the throat and changing to Red Group 56B and 56C at the base of the tube.

*Stamens.*—Two per flower, and Red-Purple Group 65A with some near White Group 155D in coloration.

*Filaments.*—Red-Purple Group 62D in coloration.

*Anthers.*—Red-Purple Group 63B in coloration.

*Pollen.*—Present in a moderate quantity and near Yellow-Green Group 154C in coloration.

*Pistil.*—Approximately 0.3 cm in length.

*Style.*—Red-Purple Group 65C in coloration.

*Stigma.*—Yellow-Green Group 150D.

*Calyx.*—Cup-shaped with an entire lobe, one per flower, rugose, approximately 0.2 cm in size, and Green Group 139C in coloration.

*Fragrance.*—Intense sweet lilac.

*Flower duration.*—Approximately 5 to 7 days on the plant with the duration commonly being influenced by the temperature and sunlight that is encountered.

*Seeds.*—None observed during observations to date.

Vegetation: Vigorous and strong.

Hardiness: Can be grown in U.S.D.A. Hardiness Zone Nos. 4 to 7. Some winter injury has been observed if grown in wet conditions.

Culture: Similar to the Dwarf Korean Lilac. Prefers well-drained soil and a sunny growing location. Generally does not well tolerate poorly drained growing conditions.

Disease/pest resistance: Has proven to be relatively free of disease and insect problems during observations to date. However, some root disease has been encountered when grown in poorly drained soil.

Landscape usage: Provides a hardy highly ornamental intensely fragrant shrub having a distinctive blossom coloration that can be grown as a specimen plant or in a mass planting. Also, the plant can be grown as a foundation planting or as an informal hedge.

What is claimed is:

1. A new and distinct *Syringa meyeri*×*Syringa microphylla* plant having the following combination of characteristics:

(a) exhibits a generally rounded to oval uniform compact dwarf growth habit, (b) forms in late spring densely packed attractive trusses of intensely sweet smelling medium pink buds that open to light pink florets that fade to almost white at full maturity, (c) is relatively free of insect and disease problems, and (d) is well suited for growing as a distinctive ornamental shrub in the landscape;

substantially as illustrated and described.

* * * * *